United States Patent [19]
Yamamoto et al.

[11] Patent Number: 5,461,233
[45] Date of Patent: Oct. 24, 1995

[54] MEDICAL X-RAY IMAGE DETECTING DEVICE AND A MEDICAL X-RAY TOMOGRAPHING APPARATUS COMPRISING SAME

[75] Inventors: Koei Yamamoto; Kazuhisa Miyaguchi; Notio Takahashi, all of Hamamatsu; Keisuke Mori, Kyoto; Masakazu Suzuki, Kyoto; Takao Makino, Kyoto, all of Japan

[73] Assignees: Kabushiki Kaisha Morita Seisakusho, Kyoto; Hamamatsu Photonics Kabushiki Kaisha, Shizuoka, both of Japan

[21] Appl. No.: 210,950

[22] Filed: Mar. 21, 1994

[30] Foreign Application Priority Data

Mar. 26, 1993 [JP] Japan .................................. 5-091986

[51] Int. Cl.$^6$ .................................. A61B 6/14; G01T 1/20
[52] U.S. Cl. .......................... 250/368; 250/366; 378/40
[58] Field of Search .................................. 250/366, 368; 378/38, 40

[56] References Cited

U.S. PATENT DOCUMENTS 4,179,100  12/1979  Sashin et al. ............................ 250/366
5,138,166   8/1992  Makino et al. .......................... 250/368

Primary Examiner—Carolyn E. Fields
Attorney, Agent, or Firm—Koda and Androlia

[57] ABSTRACT

A medical X-ray tomographing apparatus, wherein the output end surfaces of a plurality of optical fiber bundles are optically coupled to the image pickup surfaces of vertically long solid-state image pickup devices, such as one-dimensional image sensors, and the input end surfaces of a plurality of the optical fiber bundles having a vertically long cross-sectional shape being identical to that of the output end surfaces thereof are optically coupled individually to a plurality of vertically long divisions obtained by dividing the fluorescent surface of a scintillator in the width direction thereof. With this apparatus, it is not necessary to significantly contract the size of the image on the fluorescent surface, thereby remarkably reducing the number of the solid-state image pickup devices and the number of the divisions of the fluorescent surface.

7 Claims, 6 Drawing Sheets

MEDICAL X-RAY IMAGE DETECTING DEVICE AND A MEDICAL X-RAY TOMOGRAPHING APPARATUS COMPRISING SAME

BACKGROUND OF THE INVENTION

1. Field of the invention

The present invention relates to a medical X-ray image detecting device, more particularly to a device suited for detecting X-ray penetration images in a dental panoramic X-ray photographing apparatus.

2. Prior Art

Dental panoramic X-ray photographing apparatuses, which perform scanning by rotating an X-ray source and an image detecting device disposed in an opposed relation with each other along the dental arch of a patient while irradiating X-ray beams From the X-ray source, are widely used clinically to observe the arrangement of the teeth and the conditions of the dental roots of the patient.

Such X-ray panoramic photographing apparatuses are known as apparatuses capable of performing tomographing the curved section Formed along the dental arch to take the image of the dental jaw section of the patient on a single film so that the entire dental arch can be observed. In the case of these conventional apparatuses which expose X-ray penetration images to X-ray films, it is inevitably necessary to develop the X-ray films. In addition, after an image is taken along a tomographing route, it is impossible to obtain another image along a modified tomographing route. To solve these problems, a panoramic X-ray photographing apparatus has been developed recently, which obtains X-ray penetration images by using fluorescent light generated by a scintillator, introduces the light of the images into a solid-state image pickup device through an optical fiber bundle, and converts the images into electrical signals, then processes the signals so that panoramic tomographic images can be obtained, thereby reproducing the panoramic tomographic images on the display screen of a monitor unit.

In the case of the above-mentioned apparatus, the solid-state image pickup device has an image pickup surface size of about 5 mm square For example. This size is far smaller than the size of the fluorescent surface (6×150 mm for example) of the scintillator. It is very difficult to increase the size of image pickup surface of the solid-stale image pickup device. Even if possible, the cost is assumed to be excessive. Various methods have therefore been proposed to pick up visible light images formed on the fluorescent surface which is far larger than the image pickup surface of a solid-state image pickup device by using such a solid-skate image pickup device having a small image pickup surface.

Japanese Laid-open Patent Application No. 2-84942 has proposed a method, wherein the image on the fluorescent surface is contracted by using a tapered optical fiber bundle, [he input side area of which is as large as or half the area of the fluorescent surface of the scintillator and the output side area of which is as large as the area of the image pickup surface of the solid-stale image pickup device, and the image is input to the image pickup surface of the solid-state image pickup device.

In Japanese Utility Model Application No. 2-124689 (Japanese Laid-open Utility Model Publication No. 4-80507) and in its Foreign counterparts (U.S. Pat. No. 5,138,166, Ger. Pat. Application No. P41 38 659.0-35 and Fin. Pat. Application No. 915538), one of the applicants of the present invention has proposed an image detecting device which is characterized in that the fluorescent surface of a scintillator is divided in the vertical direction thereof into a plurality of rectangular units, the input end surface of each of the optical Fiber bundles of the device is attached to one of the divided rectangular surface units. the output end surface of each of the optical fiber bundles is attached to the image pickup surface of one of the image pickup devices, and the optical fiber bundles are distributed alternately right and left and laminated in the vertical direction.

In the case of the above-mentioned Japanese Laid-open Patent Application No. 2-84942, wherein the image on the Fluorescent surface of the scintillator is contracted by using the tapered optical fiber bundles and is transmitted to the image pickup surface of the solid-state image pickup device, the resolution of the image signal at the solid-state image pickup device is deteriorated because of a large image contraction ratio. Furthermore, it is difficult to taper (gradually reduce the diameter) the end of each element of the optical fiber so that the image can be contracted uniformly and significantly. Even if possible, production cost would be excessive.

Also, in the case of the above-mentioned Japanese Laid-open Utility Model Application No. 4-80507, wherein the fluorescent surface of the scintillator is divided in the vertical direction thereof into a plurality of rectangular units, a plurality (ten to several tens) of optical fiber bundles and solid state image pickup devices are necessary. It is complicated and troublesome to assemble these optical fiber bundles and image pickup devices (to attach the surfaces of the optical fiber bundles to those of the image pickup devices, for example). Production cost would also be excessive. Furthermore, since a plurality of solid-state image pickup devices are used, it is also complicated and difficult to adjust the sensitivity imbalance among the solid-state image pickup devices and to adjust the boundary regions of the solid-state image pickup devices.

As describe above, the conventional methods of introducing the light of the X-ray penetration image on the fluorescent surface of a scintillator via optical fiber bundles and picking up images by using solid-state image pickup devices having a small image pickup surface area have many problems.

SUMMARY OF THE INVENTION

To solve these problems, the present invention proposes a novel medical X-ray image detecting device which does not require to significantly contract the size of the image on the fluorescent surface and can remarkably reduce the number of divisions of the fluorescent surface. The present invention also proposes an X-ray tomographing apparatus comprising the novel image detecting device.

In view of solving the above-mentioned problems, the present invention provides a medical X-ray image detecting device comprising: a scintillator having a vertically long fluorescent image surface: a solid-state image pickup device having a vertically long image pickup surface; and optical fiber bundles whose input end surfaces and output end surfaces are optically coupled to the fluorescent image surface of the scintillator and the image pickup surface of the image pickup device respectively, wherein the input end surfaces and the output end surfaces are optically coupled to a plurality of vertically long individual divisions respectively of the fluorescent image surface and image pickup surface, the divisions being obtained by dividing the surfaces in the width direction thereof.

These objects and Features of the present invention will become apparent From the following detailed description with reference to the accompanying drawings.

DETAILED DESCRIPTION OF THE INVENTION

<EXAMPLE 1>

Figure 1:
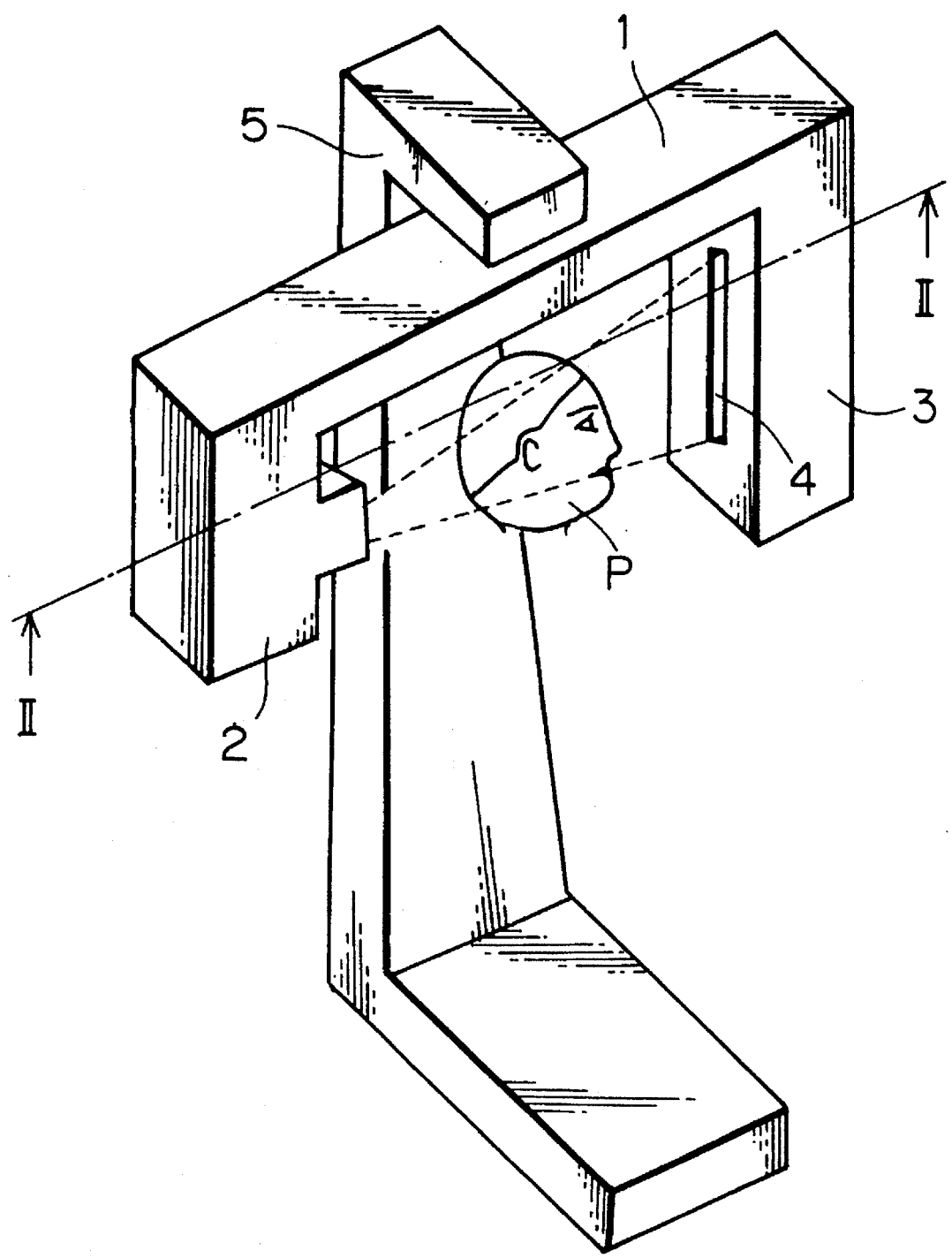
FIG. 1 is a perspective view illustrating a dental panoramic X-ray tomography apparatus equipped with a medical X-ray image detecting device according to the present invention.
Figure 2:
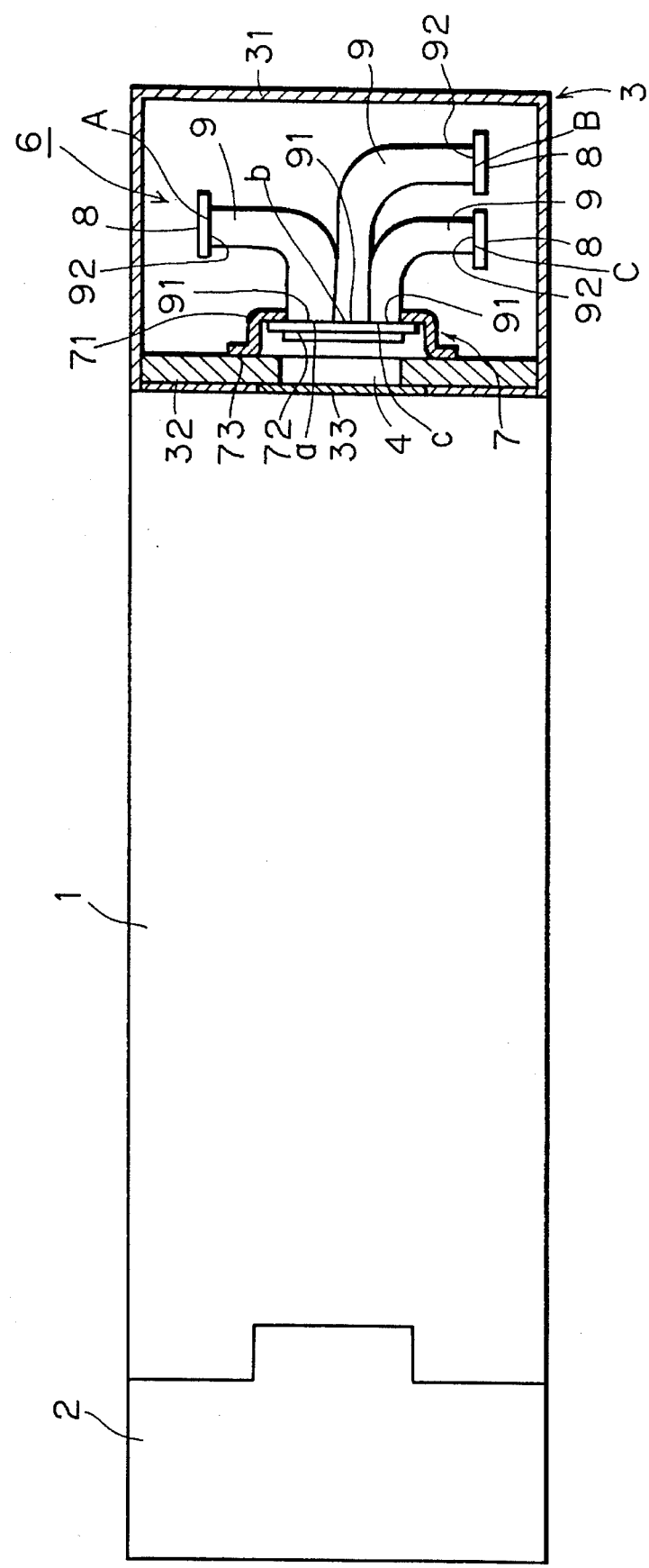
FIG. 2 is a sectional view of a first example of the present invention taken along line II—II of FIG. 1 (the interior of an X-ray source is not shown)
Figure 3:
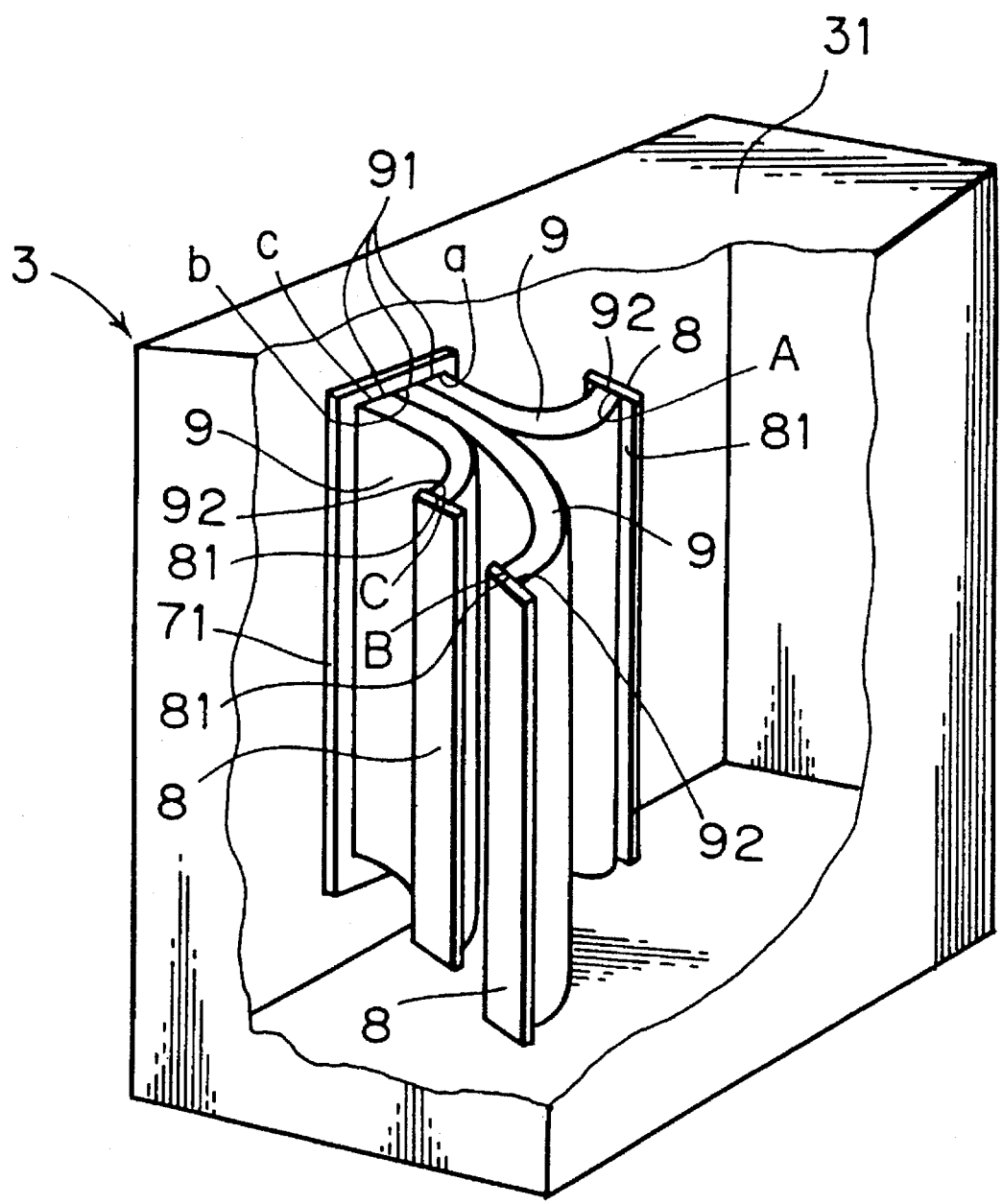
FIG. 3 is an enlarged partially cutaway view illustrating the X-ray image detecting device of the present invention incorporated in the photographic box 3 shown in FIG. 2.

Referring to FIGS. 1 to 3, numeral 1 represents a rotary arm. At both ends of the rotary arm 1, an X-ray source 2 incorporating an X-ray tube (not shown) and an photographing box 3 incorporating the X-ray image detecting device of the present invention are disposed in an opposed relation with each other. A vertically long slit 4 is disposed on the surface of the photographing box 3 facing to the X-ray source 2. The rotary arm 1 is held by a support column 5. At the time of panoramic tomographing of the dental jaw section of patient P, the position of the rotation center (not shown) of the rotary arm 1 is selected and moved appropriately by computer control or the like, and the rotary arm 1 is rotated around the rotation center so that X-ray beams irradiated from the slit (not shown) of the X-ray source 2 scan around and penetrate the entire jaw section of patient P and enter the photographing box 3 through the slit 4 thereof, as is well known in this kind of photographing apparatuses.

Referring to FIG. 2, the medical X-ray image detecting device 6 of the present invention incorporated in the photographing box 3 formed by using a steel plate 31 and equipped with an X-ray shielding plate 32 (lead plate or the like) on the Front surface thereof is held by a holder 73 so that the fluorescent plate ? of a scintillator is positioned behind the above-mentioned slit 4. The fluorescent plate 7 comprises a transparent glass substrate 71 and a fluorescent surface 72, that is, a fluorescent layer coated on the substrate 71 and used to convert the X-ray beams into visible light. In front of the slit 4, an opaque plate 33 made of aluminum or plastic is disposed to shield visible light.

Numeral 8 represents a vertically long solid-state image pickup device, that is, a CCD. To the vertically long image pickup surface 81 thereof, the output end surface 92 of an optical fiber bundle 9 having a vertically long cross-section shape being identical to that of the image pickup surface 81 is attached so that images can be Formed. Referring to FIG. 3, the output end surfaces 92 are respectively connected to the corresponding image pickup surfaces 81 of the solid-state image pickup devices 8. The optical fiber bundles 9, 9, 9 are separated from one another on their output end sides. On their input end sides, the optical fiber bundles 9, 9, 9 closely contact one another. The closely contacting input end surfaces 91, 91, 91 of the optical fiber bundles 9, 9, 9 are respectively attached to the back surface of the transparent glass substrate 71 of the fluorescent plate 7 so that the closely contacting input end surfaces 91, 91, 91 are respectively connected to the three vertically long divisions a, b, and c divided in the width direction of the fluorescent surfaces 72. In this way, the fluorescent surface 72 is optically coupled to the optical fiber bundles 9 via the substrate 71. The input end surface 91 of the optical fiber bundle 9 is identical to the output end surface 92 thereof in shape and size. As shown in FIG. 2, the optical fiber bundles 9, 9, 9 are distributed and bent right and left so that the solid-state image pickup devices 8, 8, 8 are disposed outside the irradiation and penetration range of the X-ray beams entered from the slit 4. With this arrangement, the solid-state image pickup devices can be protected from the X-ray beams.

In the First example of the medical X-ray image detecting device of the present invention having the above-mentioned structure, the X-ray beams penetrate the jaw section of patient P and enters the vertically long slit 4 to form a fluorescent image on the vertically long fluorescent surface 72 of the scintillator 7. This fluorescent image on the fluorescent surface 72 is transmitted by the optical fiber bundles 9, 9, 9 with respect to the above divisions a, b, and c, the input end surfaces of which closely contact one another and are attached to the transparent glass substrate 71. The transmitted image is converted into electrical image signals by the solid-state image pickup devices 8, 8, 8, the image pickup surfaces 81, 81 and 81 of which are attached to the output end surfaces 92, 92. 92 of the optical fiber bundles 9, 9, 9 at the divisions A, B, and C corresponding to the above end surfaces 92, 92, 92.

The image signals at the solid-state image pickup devices 8, 8, 8 are subjected to image processing (not shown) and composed by a monitor unit (not shown) to reproduce the fluorescent image formed on the above-mentioned fluorescent surface on the display screen (not shown) of the monitor unit. At this time of reproduction, in the case of panoramic tomographing, the above-mentioned rotary arm 1 rotates so that X-ray beams scan around and penetrates the jaw Section of patient P. In synchronization with the ratio of the rotation speed of the rotary arm 1 and the image feeding speed corresponding to the film feeding speed of a conventional X-ray film, an X-ray penetrated panoramic image (not shown) of the jaw section appears on the display screen. Since the sensitivity of the solid-state image pickup devices 8 is made generally high, the intensity of the X-ray can be made lower than that required for the conventional film sensing method by properly selecting fluorescent material to be coated on the fluorescent plate 7. As a result, the X-ray dose exposed to patient P can be reduced significantly. In addition, once an X-ray penetration image has been stored, the image can be modified after photographing to an image to be obtained along a different tomographing route. Furthermore, the imagine can be transmitted by Facsimile or the like without directly handling the film of the image. Moreover, the image can be subjected to image intensification processing.

A so-called one-dimensional image sensor having picture elements arranged in a row as well as a vertically long two-dimensional image sensor having picture elements arranged vertically in a plurality of rows can be used for the above-mentioned vertically long solid-state image pickup device 8. This vertically long solid-state image pickup device can be produced at lower cost and the characteristics thereof are more uniform in comparison with the vertical arrangement of a plurality of solid-state image pickup devices having square or rectangular (nearly square) image pickup surfaces.

In panoramic X-ray tomographing, sharper images can be obtained as the width of the slit 4 is narrower. Considering this matter, the size of the slit 4, that is, the size of the fluorescent surface 72 is determined. for example, the size of the fluorescent surface 72 is 6×150 mm. Its vertical length is far larger than its width; it is quite long in the vertical direction. Accordingly, by using vertically long solid-state image pickup devices 8 such as one-dimensional image pickup devices and by connecting the fluorescent surface 72 via the optical fiber bundles 9 so that the divisions of the fluorescent surface 72 are arranged in the width direction thereof, the number of the divisions of the fluorescent surface 72, the number of the optical fiber bundles 9 and the number of the solid-state image pickup devices 8 can be reduced significantly in comparison with such a case wherein the divisions of the fluorescent surface are arranged in the vertical direction as disclosed in the above-mentioned Japanese Laid-open Utility Model Publication No. 4-80507. These numbers are desired to be smaller to make assembling simpler and also to make sensitivity/boundary adjustments simpler and easier.

Additionally, since the photographing box 3 is rotated in the direction perpendicular to the longitudinal direction of the vertically long slit 4 as described above, and the vertically long image on the fluorescent surface 72 obtained by the incident X-ray from the vertically long slit 4 is swept in the same direction as that of the rotation, the effect of sensitivity imbalance among the solid-state image pickup devices 8 can be reduced in the X-ray image detecting device of the present invention wherein the vertically long solid-state image pickup devices 8 are arranged in the width direction of the fluorescent surface 72.

<EXAMPLE 2>

Figure 4:
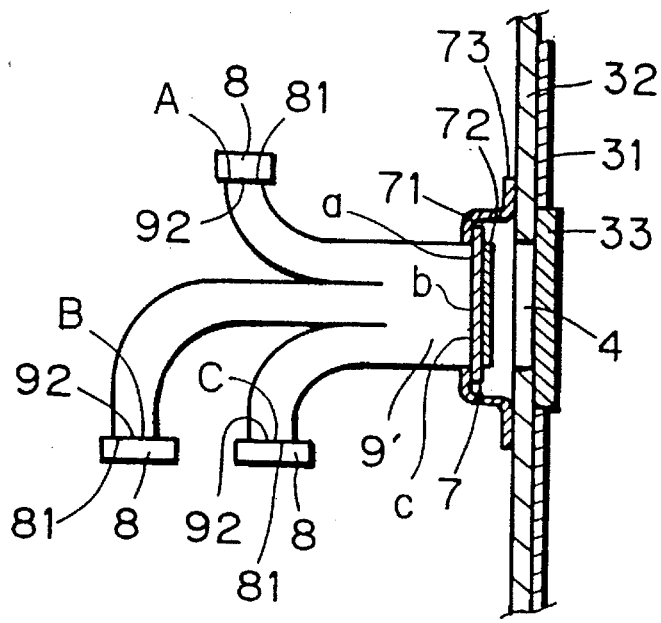
FIG. 4 is a plan view illustrating a second example of the X-ray image detecting device of the present invention.

In a second example of the X-ray image detecting device of the present invention shown in FIG. 4, although the output side of the glass fiber bundle is divided into a plurality of branches (three branches in FIG. 4), the input side thereof is integrated by disposing a single optical fiber bundle 9', instead of disposing a plurality of divided optical fiber bundles as in the case of the first example shown in FIGS. 2 and 3. Except for this arrangement, the structure of the second example shown in FIG. 4 is the same as that of the first example shown in FIGS. 2 and 3. The reference numbers shown in FIG. 4 designate the corresponding parts shown in FIGS. 2 and 3. Since this example uses only a single optical fiber bundle 9' with branches, integrated on the input side thereof, as an optical fiber bundle used to connect the fluorescent surface 72 to the solid-state image pickup devices 8, this simple structure offers remarkable advantages in attaching and assembling the optical fiber bundle 9' to the fluorescent plate 7 more simply and easily.

<EXAMPLE 3>

Figure 5:
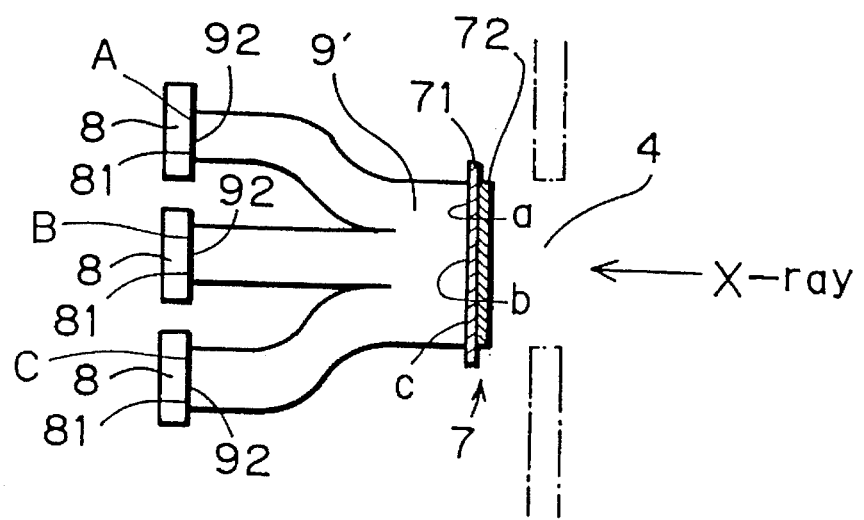
FIG. 5 is a plan view illustrating a third example of the present invention.
Figure 6:
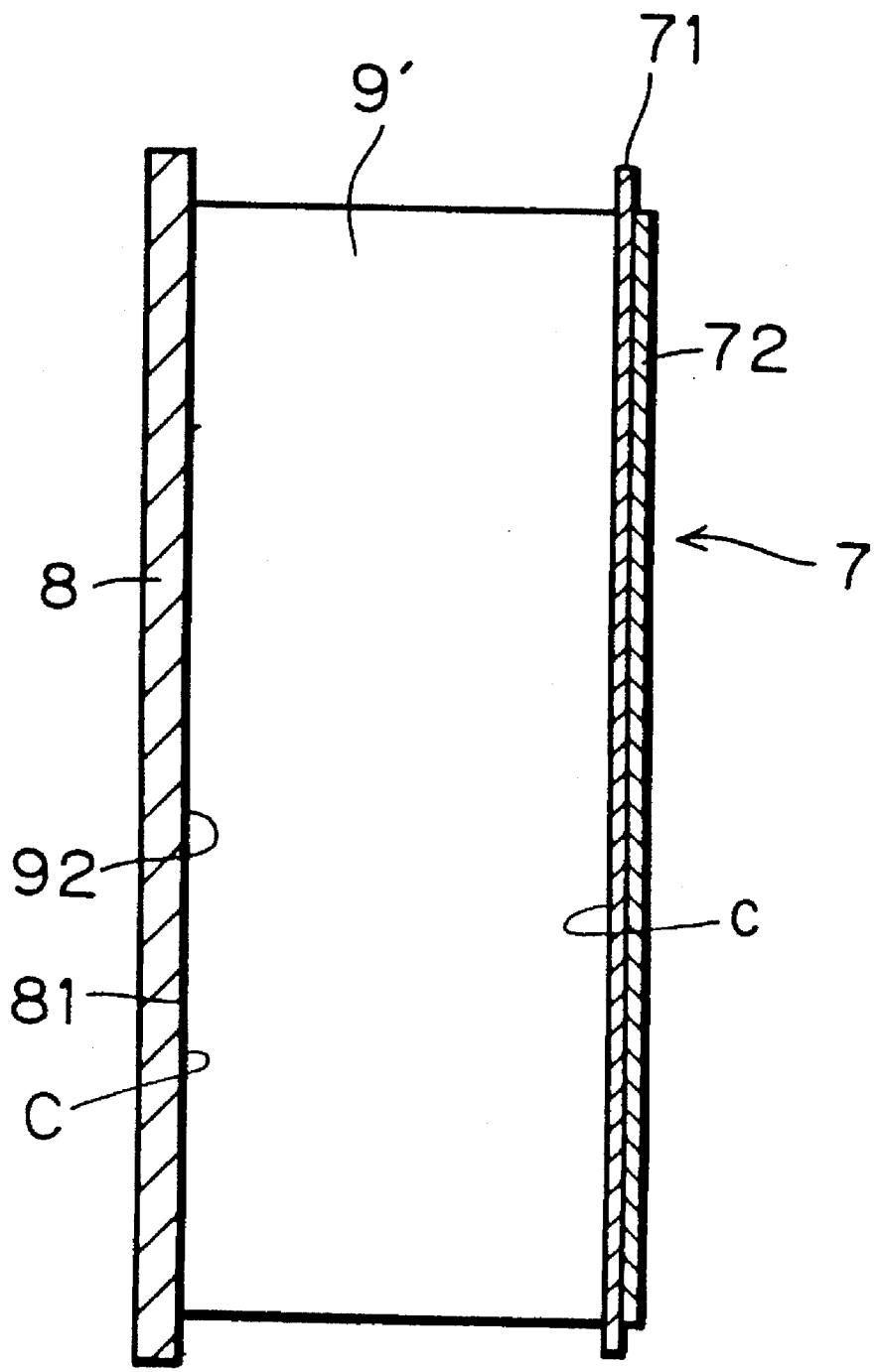
FIG. 6 is a side view illustrating the third example of the present invention of FIG. 5.

In a third example of the medical X-ray image detecting device of the present invention shown in FIGS. 5 and 6, the output end surfaces 92, 92, 92 of the optical fiber bundle 9' with branches, which are coupled to the image pickup surfaces of the three solid-state image pickup devices 8 to optically couple the fluorescent surface 72 of the scintillator to the three solid-state image pickup devices 8, are not bent or distributed right and left, unlike the second example. The output end surfaces are separated from one another and extend in the direction nearly identical to the penetration direction of the X-ray beams entered from the slit 4. Corresponding to these output end surfaces, the three solid-state image pickup devices 8 are disposed in a single plane area in the width direction. Except for this arrangement, the structure of the third example is the same as that of the second example. The reference numbers shown in FIGS. 5 and 6 designate the corresponding parts shown in FIG. 4 as well as those shown in FIGS. 2 and 3.

<EXAMPLE 4>

Figure 7:
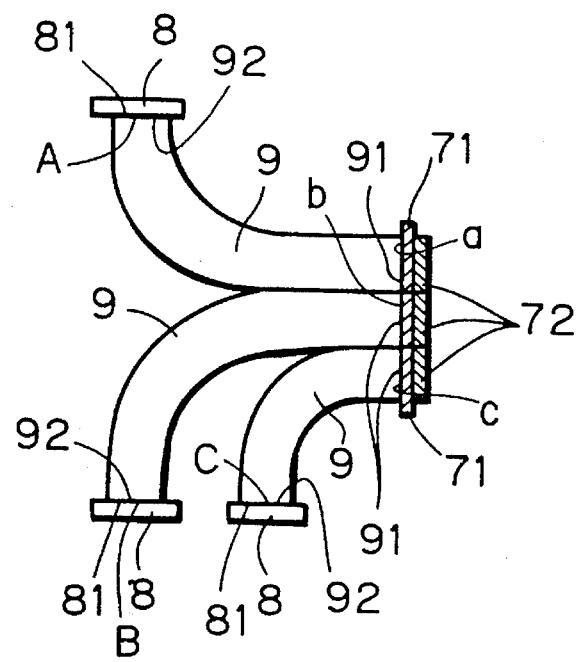
FIG. 7 is a plan view illustrating a fourth example of the present invention.

In the above-mentioned first, second and third examples, the fluorescent surface 72 of the scintillator is formed as a single fluorescent surface. In the case of a fourth example shown in FIG. 7, the fluorescent surface 72 itself is divided into a plurality of divisions (three divisions in the figure). Since the fluorescent surface 72 is divided in this way, this structure offers advantages in attaching and assembling the input end surfaces 91, 91, 91 of the optical fiber bundles 9, 9, 9 to the divisions of the fluorescent surface 72 simply and easily. However, it is necessary to properly compose images and adjust the boundary areas of the images when displaying the images on the display screen of the monitor unit. Except that the fluorescent surface 72 is divided into a plurality of divisions in the width direction as described above, the structure of the fourth example is the same as that of the first example. The reference numbers shown in FIG. 7 also designate the corresponding parts shown in FIGS. 2 and 3. Although CCDs are taken as an example of the above-mentioned solid-state image pickup devices, other devices such as photo diodes and MOS image sensors can also be used as the solid-state image pickup devices of the present invention.

<EXAMPLE 5>

Figure 8:
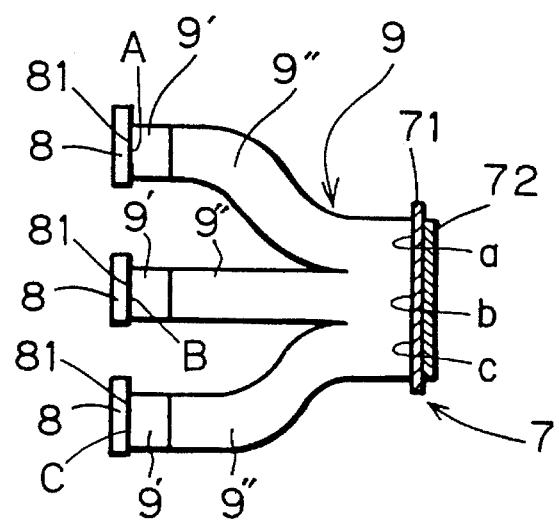
FIG. 8 is a plan view of a fifth example of the present invention.

In the case of a fifth example shown in FIG. 8. the optical fiber bundle 9 comprises two fiber parts 9' and 9" connected to each other in the longitudinal direction thereof. Except that the fiber parts 9' and 9" are separable as necessary, the structure of the fifth example is the same as that of the third example. In the case of the fifth example, when connecting the optical fiber bundle having a branched complicate shape to the solid-state image pickup devices 8, assembling can be made efficient by connecting the part 9' to the solid-state image pickup device 8 and then by connecting the assembly to the remaining part 9". Besides, in the structure wherein the parts 9' and 9" are separable, when one of the image pickup devices 8 becomes defective, only the defective image pickup device can be replaced. It is not necessary to replace the entire unit, thereby making the detecting device economical.

In the above descriptions, the vertically long solid-state image pickup device 8 capable of covering the vertical length of the vertically long fluorescent surface 72 is used and the vertically long fluorescent surface 72 is divided only in the width direction. In the medical X-ray image detecting device of the present invention, it is preferable to use the vertically long image pickup device 8 which can offer sufficient performance simply by using the fluorescent surface 72 divided only in the width direction. However, the present invention is not limited to this structure.

As the case may be, a plurality of solid-state image pickup devices having a size requiring the fluorescent surface to be divided in the width direction and also to be divided in the vertical direction into a few divisions (2 or 3 divisions) can also be used within the range of the present invention, as long as the number of divisions is far smaller than that in the case of the method disclosed by the above-mentioned Japanese Laid-open Utility Model Publication No. 4-80507 and the advantage of covering the entire fluorescent surface by using a significantly limited number of solid-state image pickup devices is retained.

Moreover, the method of contracting the fluorescent image on the fluorescent surface by using an optical fiber bundle and transmitting the image to the image pickup surface of a solid-state image pickup device can also be included in the range of the present invention, as long as the rate of contraction is small, the resolution of the solid-state image pickup device is not deteriorated substantially and the optical fiber bundle can be made without any difficulty.

In the medical X-ray image detecting device of the present invention having the structures and functions detailed above, vertically long solid-state image pickup devices, such as one-dimensional image sensors, are used. For this reason, the cost of the solid-state image detecting devices is inexpensive and the sensitivity imbalance among them is minimal. Additionally, since the number of the solid-state image pickup devices can be reduced significantly in comparison with conventional medical X-ray image detecting devices, assembling can be made far simpler and easier than in the case of the conventional detecting devices. Furthermore, the adjustment of sensitivity imbalance among solid-state image pickup devices as well as the adjustment of the boundary areas thereof can also be simplified because of simple and easy assembling. Moreover, with the present invention, it is not necessary to contract and deteriorate the resolution of the image on the fluorescent surface by using optical fiber bundles when transmitting the image to the image pickup surfaces of the solid-state image pickup devices.

We claim:

1. A medical X-ray image detecting device comprising:
   a scintillator having a vertically elongated fluorescent image surface;
   a plurality of solid-state image pickup devices each having a vertically elongated image pickup surface; and
   optical fiber bundles whose input end surfaces and output end surfaces are optically coupled to the fluorescent image surface of said scintillator and the image pickup surface of each of said plurality of said image pickup devices respectively,
   wherein the input end surfaces and the output end surfaces are optically coupled to a plurality of vertically elongated individual divisions of said fluorescent image surface and one of said image pickup surface of each of said plurality of said image pickup devices respectively, said divisions being obtained by dividing surfaces in a width direction thereof; said optical fiber bundles comprise a plurality of individual bundles and the number of said individual divisions are identical to the number of the bundles so that each input end surface and the output end surface of each individual bundle is optically coupled to one of the individual divisions of the fluorescent surface and the image pickup surface of one of said plurality of image pickup devices respectively; and said individual fiber bundles make close contact with one another on their input end sides and are branches from one another on their output sides.

2. A medical X-ray image detecting device according to claim 1, wherein each of said plurality of said image pickup devices is a vertically elongated one-dimensional sensor and said individual divisions of the fluorescent surface are formed in a single layer.

3. A medical X-ray image detecting device according to claim 1, wherein said plurality of individual bundles are integrated into a bundle having a plurality of branches extending from a middle of a base thereof, sad plurality of image pickup devices are provided in an identical number to the number of the branches, the base of the integrated bundle is disposed on the input side thereof, and the branches are disposed on the output side thereof.

4. A medical X-ray image detecting device according to claim 1, wherein each of said plurality of branches are separable.

5. A medical X-ray image detecting device according to claim 1, wherein the input end surface and the output end surface of each optical fiber bundle are almost identical to each other in shape and size.

6. A medical X-ray tomographing apparatus comprising:
   a medical X-ray image detecting device;
   a photographing box incorporating said medical X-ray image detecting device with a scintillator thereof being disposed behind a vertically elongated slit provided on an X-ray shielding plate; and
   an X-ray source being disposed at one end of a rotary arm in an opposed relation with said photographing box disposed at the other end of the rotary arm,
   said medical X-ray image detecting device comprising:
   a scintillator having a vertically elongated fluorescent image surface;
   a plurality of solid-state image pickup devices each having a vertically elongated image pickup surface; and
   optical fiber bundles with input end surfaces and output end surfaces optically coupled to the fluorescent image surface of said scintillator and the image pickup surface of one of said plurality of said image pickup devices respectively,
   wherein the input end surfaces and the output end surfaces are optically coupled to a plurality of vertically elongated individual divisions of said fluorescent image surface and the image pickup surface of one of said plurality of said image pickup devices respectively, said divisions being obtained by dividing the surfaces in a width direction thereof; said optical fiber bundles comprise a plurality of individual bundles and the number of said individual divisions are identical to the number of the bundles so that each input end surface and the output end surface of each individual bundle is optically coupled to one of said individual divisions of the fluorescent surface and the image pickup surface of one of said plurality of image pickup devices respectively; and said individual fiber bundles make close contact with one another on the input end sides and are branched from one another on their output sides.

7. A medical X-ray tomographing apparatus according to claim 6, wherein said plurality of solid state image pickup devices are disposed outside the irradiation range of the X-ray beams entered from said slit.

* * * * *